(12) United States Patent
Kramer et al.

(10) Patent No.: US 6,174,860 B1
(45) Date of Patent: Jan. 16, 2001

(54) INSECTICIDAL TOXINS AND NUCLEIC ACID SEQUENCES CODING THEREFOR

(75) Inventors: Vance Cary Kramer, Hillsborough; Michael Kent Morgan, Durham; Arne Robert Anderson, Zebulon, all of NC (US)

(73) Assignee: Novartis AG, Basel (CH)

( * ) Notice: Under 35 U.S.C. 154(b), the term of this patent shall be extended for 0 days.

(21) Appl. No.: 09/293,395

(22) Filed: Apr. 16, 1999

Related U.S. Application Data

(60) Provisional application No. 60/145,748, filed on Apr. 21, 1998, provisional application No. 60/123,500, filed on Mar. 9, 1999, and provisional application No. 60/125,525, filed on Mar. 22, 1999.

(51) Int. Cl.$^7$ .............................. A61K 38/00; C12N 5/02; C12N 5/04; C12P 21/06
(52) U.S. Cl. ..................... 514/12; 536/23.11; 435/69.1; 435/410; 435/412
(58) Field of Search ............................... 435/252.3, 69.1, 435/419, 254.2, 412; 536/23.1

(56) References Cited

FOREIGN PATENT DOCUMENTS

| 93/03154 | * | 7/1992 | (WO) . |
|---|---|---|---|
| WO 95/00647 | * | 1/1995 | (WO) . |
| 96/38547 | * | 5/1996 | (WO) . |
| WO 97/17432 | * | 5/1997 | (WO) . |
| WO 98/08388 | * | 3/1998 | (WO) . |
| WO 98/08932 | * | 3/1998 | (WO) . |
| WO 99/03328 | * | 1/1999 | (WO) . |

OTHER PUBLICATIONS

Ivey et al. Accession U56090, Dec. 1996.*
Smith, A. Accession AC004083, Jan. 1998.*
Ivey et al. Acession U56090, Dec. 1996.*
Smith, A. Accession AC004083, Jan. 1998.*
Marra et al. Acession AA895852, Apr. 1998.*
Hillier et al. Acession T74981, Mar. 1995.*
Ivey et al. Acession U56090, Dec. 1996.*
Cho, Y. Acession X89403, Nov. 1996.*
Dante et al. Acession AC002066, May 1997.*
Geisel et al. Acession AC002069, May 1997.*
Dante et al. Acession AC002066, May 1997.*
Pedersen, B. Acession L26570, Feb. 1996.*
Hillier et al. Acession N99108, Apr. 1996.*
Hudspeth et al. Acession V00705 J01525, Oct. 1996.*
Cho, Y. Acession X89403, Nov. 1996.*
Bintrim, S.B., Dissertation entitled, "A Study of the Crystalline Inclusion Proteins of *Photohabdus luminescens*" (1994).*
Bowen, D.J., Dissertation entitled, "Characterization of a high molecular weight insecticidal protein complex produced by the entomopathogenic bacterum *Photohabdus liminescens*" (1995).*
Forst et al., "Molecular Biology of the Symbiotic–Pathogenic Bacteria Xenorhabdus spp. and Photorhabdus spp.", *Microbiological Reviews* 60(1):21–43 (Mar. 1996).*
Forst et al., "Xenorhabdus and Photorhabdus ssp.: Bugs That Kill Bugs", *Annu. Rev Microbiol.*, 51: 47–72 (1997).*
Hammock et al., "Expression and effects of the juvenile hormone esterase in a baculovirus vector", *Nature* 344: 458–461 (1990).*
Vermunt et al., "Cloning and Sequence Analysis of cDNA Encoding a Putative Juvenile Hormone Esterase from the Colorado Potato Beetle" *Insect Biochem. Molec. Biol.* 27(11):919–928 (1997).*
Stemmer, *Nature*, 370:389–391(1994).*
Bowen et al., *Science*, 280:2129–2132(1998).*

\* cited by examiner

*Primary Examiner*—Ponnathapu Achutamurthy
*Assistant Examiner*—Christian Fronda
(74) *Attorney, Agent, or Firm*—J. Timothy Meigs; Larry W. Stults

(57) ABSTRACT

Novel nucleic acid sequences isolated from *Xenorhabdus nematophilus, Xenorhabdus poinarii*, and *Photorhabdus luminescens*, whose expression results in novel insecticidal toxins, are disclosed herein. The invention also discloses compositions and formulations containing the insecticidal toxins that are capable of controlling insect pests. The invention is further drawn to methods of making the toxins and to methods of using the nucleotide sequences, for example in microorganisms to control insect pests or in transgenic plants to confer insect resistance.

23 Claims, No Drawings

INSECTICIDAL TOXINS AND NUCLEIC ACID SEQUENCES CODING THEREFOR

This application claims the benefit of U.S. Provisional Application Ser. No. 60/145,748 filed Apr. 21, 1998; U.S. Provisional Application Ser. No. 60/123,500, filed Mar. 9, 1999; and U.S. Provisional Application Ser. No. 60/125,525, filed Mar. 22, 1999. The disclosure of each the aforementioned applications is hereby expressly incorporated by reference in its entirety into the instant disclosure.

FIELD OF THE INVENTION

The invention relates to novel toxins from *Xenorhabdus nematophilus*, *Xenorhabdus poinarii*, and *Photorhabdus luminescens*, nucleic acid sequences whose expression results in said toxins, and methods of making and methods of using the toxins and corresponding nucleic acid sequences to control insects.

BACKGROUND OF THE INVENTION

Insect pests are a major cause of crop losses. Solely in the U.S., about $7.7 billion are lost every year due to infestation by various genera of insects. In addition to losses in field crops, insect pests are also a burden to vegetable and fruit growers, to producers of ornamental flowers, and they are a nuisance to gardeners and home owners.

Insect pests are mainly controlled by intensive applications of chemical insecticides, which are active through inhibition of insect growth, prevention of insect feeding or reproduction, or death of the insects. Good insect control can thus be reached, but these chemicals can sometimes also affect other, beneficial insects. Another problem resulting from the wide use of chemical pesticides is the appearance of resistant insect varieties. This has been partially alleviated by various resistance management strategies, but there is an increasing need for alternative pest control agents. Biological insect control agents, such as *Bacillus thuringiensis* strains expressing insecticidal toxins like δ-endotoxins, have also been applied with satisfactory results, offering an alternative or a complement to chemical insecticides. Recently, the genes coding for some of these δ-endotoxins have been isolated and their expression in heterologous hosts have been shown to provide another tool for the control of economically important insect pests. In particular, the expression of insecticidal toxins in transgenic plants, such as *Bacillus thuringiensis* δ-endotoxins, has provided efficient protection against selected insect pests, and transgenic plants expressing such toxins have been commercialized, allowing farmers to reduce applications of chemical insect control agents. Yet, even in this case, the development of resistance remains a possibility and only a few specific insect pests are controllable. Consequently, there remains a long-felt but unfulfilled need to discover new and effective insect control agents that provide an economic benefit to farmers and that are environmentally acceptable.

SUMMARY OF THE INVENTION

The present invention addresses the long-standing need for novel insect control agents. Particularly needed are control agents that are targeted to economically important insect pests and that efficiently control insect strains resistant to existing insect control agents. Furthermore, agents whose application minimizes the burden on the environment are desirable.

In the search for novel insect control agents, certain classes of nematodes from the genera Heterorhabdus and Steinemema are of particular interest because of their insecticidal properties. They kill insect larvae and their offspring feed in the dead larvae. Indeed, the insecticidal activity is due to symbiotic bacteria living in the nematodes. These symbiotic bacteria are Photorhabdus in the case of Heterorhabdus and Xenorhabdus in the case of Steinemema.

The present invention is drawn to nucleotide sequences isolated from *Xenorhabdus nematophilus*, and nucleotide sequences substantially similar thereto, whose expression result in insecticidal toxins that are highly toxic to economically important pests, particularly plant pests. The invention is further drawn to the insecticidal toxin resulting from the expression of the nucleotide sequence, and to compositions and formulations containing the insecticidal toxin, that are capable of inhibiting the ability of insect pests to survive, grow or reproduce, or of limiting insect-related damage or loss in crop plants. The invention is further drawn to a method of making the toxin and to methods of using the nucleotide sequence, for example in microorganisms to control insects or in transgenic plants to confer insect resistance, and to a method of using the toxin, and compositions and formulations comprising the toxin, for example applying the toxin, composition or formulation to insect infested areas, or to prophylactically treat insect susceptible areas or plants to confer protection or resistance against harmful insects.

The novel toxin is highly insecticidal against *Plutella xylostella* (diamondback moth), an economically important insect pest. The toxin can be used in multiple insect control strategies, resulting in maximal efficiency with minimal impact on the environment.

According to one aspect, the present invention provides an isolated nucleic acid molecule comprising: (a) a nucleotide sequence substantially similar to a nucleotide sequence selected from the group consisting of: nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14; or (b) a nucleotide sequence isocoding with the nucleotide sequence of (a); wherein expression of said nucleic acid molecule results in at least one toxin that is active against insects. In one embodiment of this aspect, the nucleotide sequence is isocoding with a nucleotide sequence substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. Preferably, the nucleotide sequence is substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. More preferably, the nucleotide sequence encodes an amino acid sequence selected from the group consisting of SEQ ID NOs:2, 3, 5, 7, 9, 11, 13, and 15. Most preferably, the nucleotide sequence comprises nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14. In another embodiment, the nucleotide sequence comprises the approximately 3.0 kb DNA fragment comprised in pCIB9369 (NRRL B-21883).

According to a preferred embodiment, the toxins resulting from expression of the nucleic acid molecules of the invention have activity against *Plutella xylostella*.

In another aspect, the present invention provides an isolated nucleic acid molecule comprising a 20, 25, 30, 35, 40, 45, or 50 (preferably 20) base pair nucleotide portion identical in sequence to a respective consecutive 20, 25, 30, 35, 40, 45, or 50 (preferably 20) base pair nucleotide portion of a nucleotide sequence selected from the group consisting of: nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14, wherein expression of said nucleic acid molecule results in at least one toxin that is active against insects.

The present invention also provides a chimeric gene comprising a heterologous promoter sequence operatively linked to a nucleic acid molecule of the invention. Further, the present invention provides a recombinant vector comprising such a chimeric gene. Still further, the present invention provides a host cell comprising such a chimeric gene. A host cell according to this aspect of the invention may be a bacterial cell a yeast cell, or a plant cell, preferably a plant cell. Even further, the present invention provides a plant comprising such a plant cell. Preferably, the plant is maize.

In yet another aspect, the present invention provides toxins produced by the expression of DNA molecules of the present invention. According to a preferred embodiment, the toxins of the invention have activity against *Plutella xylostella.*

In one embodiment, the toxins are produced by the *E. coli* strain designated as NRRL accession number B-21883.

In another embodiment, a toxin of the invention comprises an amino acid sequence selected from the group consisting of: SEQ ID NOs:2, 3, 5, 7, 9, 11, 13, and 15.

The present invention also provides a composition comprising an insecticidally effective amount of a toxin according to the invention.

In another aspect, the present invention provides a method of producing a toxin that is active against insects, comprising: (a) obtaining a host cell comprising a chimeric gene, which itself comprises a heterologous promoter sequence operatively linked to the nucleic acid molecule of the invention; and (b) expressing the nucleic acid molecule in the cell, which results in at least one toxin that is active against insects.

In a further aspect, the present invention provides a method of producing an insect-resistant plant, comprising introducing a nucleic acid molecule of the invention into the plant, wherein the nucleic acid molecule is expressible in the plant in an effective amount to control insects. According to a preferred embodiment, the insects are *Plutella xylostella.*

In a still further aspect, the present invention provides a method of controlling insects comprising delivering to the insects an effective amount of a toxin according to the present invention. According to a preferred embodiment, the insects are *Plutella xylostella.* Preferably, the toxin is delivered to the insects orally.

Yet another aspect of the present invention is the provision of a method for mutagenizing a nucleic acid molecule according to the present invention, wherein the nucleic acid molecule has been cleaved into population of double-stranded random fragments of a desired size, comprising: (a) adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with a polymerase under conditions which result in the annealing of the single-stranded fragments at the areas of identity to form pairs of annealed fragments, the areas of identity being sufficient for one member of a pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

DEFINITIONS

"Activity" of the toxins of the invention is meant that the toxins function as orally active insect control agents, have a toxic effect, or are able to disrupt or deter insect feeding, which may or may not cause death of the insect. When a toxin of the invention is delivered to the insect, the result is typically death of the insect, or the insect does not feed upon the source that makes the toxin available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, mRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

A "nucleic acid molecule" or "nucleic acid sequence" is a linear segment of single- or double-stranded DNA or RNA that can be isolated from any source. In the context of the present invention, the nucleic acid molecule is preferably a segment of DNA. "ORF" means open reading frame.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C with washing in 2×SSC, 0.1% SDS at 50° C, more desirably in 7% sodium dodecyl sulfate (SDS), 0.5 M $NaPO_4$, 1 mM EDTA at 50° C. with washing in 1×SSC, 0.1% SDS at 50° C, more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C., with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gin; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

BRIEF DESCRIPTION OF THE SEQUENCES IN THE SEQUENCE LISTING

SEQ ID NO:1 is the sequence of the approximately 3.0 kb DNA fragment comprised in *Xenorhabdus nematophilus* clone pCIB9369, which comprises the following ORFs at the specified nucleotide positions:

| Name | Start | End |
|------|-------|-----|
| orf1 | 569 | 979 |
| orf2 | 1045 | 2334 |

SEQ ID NO:2 is the sequence of the ~15 kDa protein encoded by orf1 of clone pCIB9369.

SEQ ID NO:3 is the sequence of the ~47.7 kDa Juvenile Hormone Esterase-like protein encoded by orf2 of clone pCIB9369.

SEQ ID NO:4 is the DNA sequence of orf1 of *Xenorhabdus nematophilus* clone pCIB9381.

SEQ ID NO:5 is the sequence of the protein encoded by orf1 of clone pCIB9381.

SEQ ID NO:6 is the DNA sequence of orf2 of *Xenorhabdus nematophilus* clone pCIB9381.

SEQ ID NO:7 is the sequence of the Juvenile Hormone Esterase-like protein encoded by orf2 of clone pCIB9381.

SEQ ID NO:8 is the DNA sequence of orf1 of *Xenorhabdus poinarii* clone pCIB9354.

SEQ ID NO:9 is the sequence of the protein encoded by orf1 of clone pCIB9354.

SEQ ID NO:10 is the DNA sequence of orf2 of *Xenorhabdus poinarii* clone pCIB9354.

SEQ ID NO:11 is the sequence of the Juvenile Hormone Esterase-like protein encoded by orf2 of clone pCIB9354.

SEQ ID NO:12 is the DNA sequence of orf1 of *Photorhabdus luminescens* clone pCIB9383-21.

SEQ ID NO:13 is the sequence of the protein encoded by orf1 of clone pCIB9383-21.

SEQ ID NO:14 is the DNA sequence of orf2 of *Photorhabdus luminescens* clone pCIB9383-21.

SEQ ID NO:15 is the sequence of the Juvenile Hormone Esterase-like protein encoded by orf2 of clone pCIB9383-21.

DEPOSITS

The following material has been deposited with the Agricultural Research Service, Patent Culture Collection (NRRL), 1815 North University Street, Peoria, Ill. 61604, under the terms of the Budapest Treaty on the International Recognition of the Deposit of Microorganisms for the Purposes of Patent Procedure. All restrictions on the availability of the deposited material will be irrevocably removed upon the granting of a patent.

| Clone | Accession Number | Date of Deposit |
|-------|------------------|-----------------|
| pCIB9369 | NRRL B-21883 | November 12, 1997 |
| pCIB9354 | NRRL B-30109 | February 25, 1999 |
| pCIB9381 | NRRL B-30110 | February 25, 1999 |
| pCIB9383-21 | NRRL B-30111 | February 25, 1999 |

DETAILED DESCRIPTION OF THE INVENTION

Novel Nucleic Acid Sequences whose Expression Results in Insecticidal Toxins

This invention relates to nucleic acid sequences whose expression results in novel toxins, and to the making and using of the toxins to control insect pests. The nucleic acid sequences are isolated from *Xenorhabdus nematophilus*, *Xenorhabdus poinarii*, and *Photorhabdus luminescens*, members of the Enterobacteriaceae family. Xenorhabdus are symbiotic bacteria of nematodes of the genus Steinemema. Photorhabdus are symbiotic bacteria of nematodes of the genus Heterorhabditis. The nematodes colonize insect larva, kill them, and their offspring feed on the dead larvae. The insecticidal activity is actually produced by the symbiotic Xenorhabdus and Photorhabdus bacteria. The inventors are the first to isolate the nucleic acid sequences of the present invention. The expression of the nucleic acid sequences of the present invention results in toxins that can be used to control Lepidopteran insects such as *Plutella xylostella* (Diamondback Moth).

A nucleotide sequence of the present invention in clone pCIB9369 is characterized by an approximately 3.0 kb DNA fragment deposited pursuant to the Budapest Treaty for Patent Deposits under Accession Number NRRL B-21883. The sequence of this DNA fragment is set forth in SEQ ID NO:1. Two open reading frames (ORF) are present in SEQ ID NO:1 (nucleotides 569–979 and nucleotides 1045–2334, respectively), coding for proteins of predicted sizes of 15 kDa and 47.7 kDa (SEQ ID NOs:2 and 3, respectively). The two ORFs are arranged in an operon-like structure. A search for known sequences showing homology to each individual ORF using the UWGCG Blast and Gap programs does not reveal any significant match for ORF #1 and reveals 21% identity between ORF #2 and *Bacillus thuringensis* cry3A protein, which is not considered to be significant in the art. A Gap analysis of the protein encoded by ORF #2 of pCIB9369 by the Blast program identifies 30.6% AA identity and 44.1% AA similarity to a juvenile hormone esterase-related protein (GenBank accession 2921553; Henikoff et al., *PNAS USA* 89: 10915–10919 (1992)). The nucleotide sequence of the present invention is also compared to known *Xenorhabdus nematophilus* sequences encoding the insecticidal toxin toxb4 (WO 95/00647), but no significant homology is found. The 3.0 kb DNA fragment is also compared to the nucleotide sequence published in WO 98/08388. Twenty-two sequences of 60 nucleotides each (60-mers) from the 38.2 kb DNA fragment described in WO 98/08388 are compared to the 3.0 kb DNA fragment of the present invention using the UWGCG Gap program. The nucleotide sequence of the first 60-mer starts at base 1 of the 38.2 kb DNA fragment and the other 60-mers are located at approximately 2.0 kb intervals. Each of the 22 sequences as well as their complementary sequences are tested. The highest percent of identity between the 3.0 kb DNA fragment of the present invention and one of these 60-mers is 53%, which is not a significant homology. Furthermore, five different DNA fragments of the 38.2 kb sequence are tested for hybridization to the 3.0 kb fragment of the present invention by Southern blot analysis. None of them reveal a positive hybridization signal.

The nucleotide sequences of pCIB9381, pCIB9354, and pCIB9383-21 also reveal two open reading frames in each of these clones. The nucleotide sequences of the two ORFs in each of pCIB9381 and pCIB9383-21 are highly homologous to those in pCIB9369. Hence, the ORF #2 proteins of pCIB9381 and pCIB9383-21 have essentially the same homology to the juvenile hormone esterase-related protein as does the ORF #2 protein of pCIB9369. The nucleotide sequence of ORF #1 of pCIB9354 is 77% identical to the nucleotide sequence of ORF #1 of pCIB9369, and the nucleotide sequence of ORF #2 of pCIB9354 is 79% identical to the nucleotide sequence of ORF #2 of pCIB9369. The ORF #2 protein of pCIB9354 also has homology to the juvenile hormone esterase-related protein (29.2% M identity and 42.2% AA similarity).

In a preferred embodiment, the invention encompasses a nucleotide sequence substantially similar to nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14, whose expression results in an insecticidal toxin. The present invention also encompasses recombinant vectors comprising the nucleic acid sequences of this invention. In such vectors, the nucleic acid sequences are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *E. coli*. In another embodiment, host cells for such recombinant vectors are endophytes or epiphytes. A preferred host cell for such vectors is a eukaryotic cell, such as a yeast, a plant cell, or an insect cell. Plant cells such as maize cells are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of such host cells. In one, such host cells are prokaryotic cells. In a preferred embodiment, such host cells are eukaryotic cells, such as yeast cells, insect cells, or plant cells. In a most preferred embodiment, the host cells are plant cells, such as maize cells.

The nucleotide sequences of the invention can be isolated using the techniques described in the examples below, or by PCR using the sequences set forth in the sequence listing as the basis for constructing PCR primers. For example, oligonucleotides having the sequence of approximately the first and last 20–25 consecutive nucleotides of orf1 of SEQ ID NO:1 (e.g., nucleotides 569–588 and 957–976 of SEQ ID NO:1) can be used as PCR primers to amplify the orf1 coding sequence (nucleotides 569–976 of SEQ ID NO:1) directly from the source strain (*Xenorhabdus nematophilus* strain ATCC 19061). The other gene sequences of the invention can likewise be amplified by PCR from the respective source strains using the ends of the coding sequences set forth in the sequence listing as the basis for PCR primers.

In another preferred embodiment, the insecticidal toxins comprise at least one polypeptide encoded by a nucleotide sequence of the invention. The molecular weight of an insecticidal toxin according to the invention is larger than 6,000, as determined by size fractionation experiments. After treatment with proteinase K, only a minimal decrease in insecticidal activity is observed in the insect bioassay, indicating that the insecticidal toxins are substantially resistant to proteinase K treatment. The insecticidal toxins retain their insecticidal activity after being stored at 22° C. or at 4° C. for 2 weeks. They also retains their insecticidal activity after being freeze dried and stored at 22° C. for 2 weeks. The insecticidal toxins are also still active after incubation for 5 minutes at 60° C., but they loses their insecticidal activity after incubation for 5 minutes at 100° C. or 80° C.

In further embodiments, the nucleotide sequences of the invention can be modified by incorporation of random mutations in a technique known as in-vitro recombination or DNA shuffling. This technique is described in Stemmer et al., Nature 370: 389–391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or range of target insect pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, *Xenorhabdus nematophilus, Xenorhabdus poinarii,* or *Photorhabdus luminescens* cells comprising modifications of at least one nucleotide sequence of this invention at its chromosomal location are described. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to *Xenorhabdus nematophilus, Xenorhabdus poinarii,* or *Photorhabdus luminescens* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in-vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces and Xanthomonas. Symbiotic fungi, such as Trichoderma and Gliocladium are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli* either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely for example, on yeast vectors and include the use of Pichia, Saccharomyces and Kluyveromyces (Sreekrishna, In: Industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et al., Biotechnology 8:135–139 (1990)).

In another preferred embodiment, at least one of the described nucleotide sequences is transferred to and expressed in *Pseudomonas fluorescens* strain CGA267356 (described in the published application EU 0 472 494 and in WO 94/01561) which has biocontrol characteristics. In another preferred embodiment, a nucleotide sequence of the invention is transferred to *Pseudomonas aureofaciens* strain 30-84 which also has biocontrol characteristics. Expression in heterologous biocontrol strains requires the selection of vectors appropriate for replication in the chosen host and a suitable choice of promoter. Techniques are well known in the art for expression in gram-negative and gram-positive bacteria and fungi.

Expression of the Nucleotide Sequences in Plant Tissue

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, Arabidopsis, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least 35% about GC content, preferably more than about 45%, more preferably more than about 50%, and most preferably more than about 60%. Microbial nucleotide sequences which have low GC contents may express poorly in plants due to the existence of ATTTA motifs which may destabilize messages, and ATAMA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

For efficient initiation of translation, sequences adjacent to the initiating methionine may require modification. For example, they can be modified by the inclusion of sequences known to be effective in plants. Joshi has suggested an appropriate consensus for plants (NAR 15: 6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CaMV 35S and 19S promoters. The nucleotide sequences of this invention can also be expressed under the regulation of promoters that are chemically regulated. This enables the insecticidal toxins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells which need to synthesize the insecticidal toxins to kill the invading insect pest. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 to Ciba-Geigy). A preferred stem specific promoter is that described in U.S. Pat. No. 5,625,136 (to Ciba-Geigy) and which drives expression of the maize trpA gene.

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tm1 from CaMV, E9 from rbcS). Any available terminator known to function in plants can be used in the context of this invention.

Numerous other sequences can be incorporated into expression cassettes described in this invention. These include sequences which have been shown to enhance expression such as intron sequences (e.g. from Adh1 and bronze1) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093–1096 (1986)). For both direct gene transfer and Agrobacterium-mediated transfer, transformation is usually (but not necessarily) undertaken with a selectable marker which may provide resistance to an antibiotic (kanamycin, hygromycin or methotrexate) or a herbicide (basta). Examples of such markers are neomycin phosphotransferase, hygromycin phosphotransferase, dihydrofolate reductase, phosphinothricin acetyltransferase, 2,2-dichloroproprionic acid dehalogenase, acetohydroxyacid synthase, 5-enolpyruvyl-shikimate-phosphate synthase, haloarylnitrilase, protoporhyrinogen oxidase, acetyl-coenzyme A carboxylase, dihydropteroate synthase, chloramphenicol acetyl transferase, and β-glucuronidase. The choice of selectable or screenable marker for plant transformation is not, however, critical to the invention.

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., BioTechniques 4:320–334 (1986)), electroporation (Riggs et al., Proc. Natl. Acad. Sci. USA 83:5602–5606 (1986), Agrobacterium-mediated transformation (Hinchee et al., Biotechnology 6:915–921 (1988); See also, Ishida et al., Nature Biotechnology 14:745–750 (June 1996) for maize transformation), direct gene transfer (Paszkowski et al., EMBO J. 3.2717–2722 (1984); Hayashimoto et al., Plant Physiol. 93:857–863 (1990)(rice)), and ballistic particle acceleration using devices available from Agracetus, Inc., Madison, Wisconsin and Dupont, Inc., Wilmington, Del. (see, for example, Sanford et al., U.S. Pat. No. 4,945,050; and McCabe et al., Biotechnology 6.923–926 (1988)). See also, Weissinger et al., Annual Rev. Genet. 22:421–477 (1988); Sanford et al., Particulate Science and Technology 5.27–37 91987)(onion); Svab et al., Proc. Natl. Acad. Sci. USA 87: 8526–8530 (1990) (tobacco chloroplast); Christou et al., Plant Physiol. 87:671–674 (1988)(soybean); McCabe et al., Bio/Technology 6.923–926 (1988)(soybean); Klein et al., Proc. Natl. Acad. Sci. USA, 85:4305–4309 (1988)(maize); Klein et al., Bio/Technology 6:559–563 (1988) (maize); Klein et al., Plant Physiol. 91:440–444 (1988) (maize); Fromm et al., Bio/Technology 8:833–839 (1990); and Gordon-Kamm et al., Plant Cell 2: 603–618 (1990) (maize); Koziel et al., Biotechnology 11: 194–200 (1993) (maize); Shimamoto et al., Nature 338: 274–277 (1989) (rice); Christou et al., Biotechnology 9: 957–962 (1991) (rice); Datta et al., Bio/Technology 8:736–740 (1990) (rice); European Patent Application EP 0 332 581 (orchardgrass and other Pooideae); Vasil et al., Biotechnology 11: 1553–1558 (1993) (wheat); Weeks et al., Plant Physiol. 102: 1077–1084 (1993) (wheat); Wan et al., Plant Physiol. 104: 37–48 (1994) (barley); Jahne et al., Theor. Appl. Genet. 89:525–533 (1994)(barley); Umbeck et al., Bio/Technology 5: 263–266 (1987) (cotton); Casas et al., Proc. Natl. Acad. Sci. USA 90:11212–11216 (Dec. 1993) (sorghum); Somers et al., Bio/Technology 10:1589–1594 (Dec. 1992) (oat); Torbert et al., Plant Cell Reports 14:635–640 (1995) (oat); Weeks et al., Plant Physiol. 102:1077–1084 (1993) (wheat); Chang et al., WO 94/13822 (wheat) and Nehra et al., The Plant Journal 5.285–297 (1994) (wheat). A particularly preferred set of embodiments for the introduction of recombinant DNA molecules into maize by microprojectile bombardment can be found in Koziel et al., Biotechnology 11: 194–200 (1993), Hill et al., Euphytica 85:119–123 (1995) and Koziel et al., Annals of the New York Academy of Sciences 792:164–171 (1996). An additional preferred embodiment is the protoplast transformation method for maize as disclosed in EP 0 292 435. Transformation of plants can be undertaken with a single DNA species or multiple DNA species (i.e. co-transformation) and both these techniques are suitable for use with the peroxidase coding sequence.

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917). Previously, this marker had been used successfully for high-frequency transformation of the plastid genome of the green alga *Chlamydomonas reinhardtii* (Goldschmidt-Clermont, M. (1991) *Nucl. Acids Res.* 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Formulation of Insecticidal Compositions

The invention also includes compositions comprising at least one of the insecticidal toxins of the present invention. In order to effectively control insect pests such compositions preferably contain sufficient amounts of toxin. Such amounts vary depending on the crop to be protected, on the particular pest to be targeted, and on the environmental conditions, such as humidity, temperature or type of soil. In a preferred embodiment, compositions comprising the insecticidal toxins comprise host cells expressing the toxins without additional purification. In another preferred embodiment, the cells expressing the insecticidal toxins are lyophilized prior to their use as an insecticidal agent. In another embodiment, the insecticidal toxins are engineered to be secreted from the host cells. In cases where purification of the toxins from the host cells in which they are expressed is desired, various degrees of purification of the insecticidal toxins are reached.

The present invention further embraces the preparation of compositions comprising at least one insecticidal toxin of the present invention, which is homogeneously mixed with one or more compounds or groups of compounds described herein. The present invention also relates to methods of treating plants, which comprise application of the insecticidal toxins or compositions containing the insecticidal toxins, to plants. The insecticidal toxins can be applied to the crop area in the form of compositions or plant to be treated, simultaneously or in succession, with further compounds. These compounds can be both fertilizers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying insecticidal toxins of the present invention is by spraying to the environment hosting the insect pest like the soil, water, or foliage of plants. The number of applications and the rate of application depend on the type and intensity of infestation by the insect pest. The insecticidal toxins can also penetrate the plant through the roots via the soil (systemic action) by impregnating the locus of the plant with a liquid composition, or by applying the compounds in solid form to the soil, e.g. in granular form (soil application). The insecticidal toxins may also be applied to seeds (coating) by impregnating the seeds either with a liquid formulation containing insecticidal toxins, or coating them with a solid formulation. In special cases, further types of application are also possible, for example, selective treatment of the plant stems or buds. The insecticidal toxins can also be provided as bait located above or below the ground.

The insecticidal toxins are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances.

The formulations, compositions or preparations containing the insecticidal toxins and, where appropriate, a solid or liquid adjuvant, are prepared in known manner, for example by homogeneously mixing and/or grinding the insecticidal toxins with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Suitable surface-active compounds are nonionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohovethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutyinapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one C8–C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

A. Isolation Of Nucleotide Sequences Whose Expression Results In Toxins Active Against Lepidopteran Insects Example 1

Growth of Xenorhabdus and Photorhabdus Strains

For insect bioassays, the following strains are grown in nutrient broth at 25° C. for 3 days in the growth media recommended by ATCC. For DNA isolation, the cultures are grown for 24 hr under the same conditions.

*Xenorhabdus nematophilus* strain ATCC 19061
*Xenorhabdus nematophilus* strain Ps1 (a USDA isolate)
*Xenorhabdus poinarii* strain ATCC 49122
*Photorhabdus luminescens* strain Ps5 (a USDA isolate)

Example 2

Insect Bioassay

*Plutella xylostella* (Px) bioassays are performed by aliquoting 50 µl of each *E. coli* culture on the solid artificial *P. xylostella* diet (Biever and Boldt, Annals of Entomological Society of America,1971; Shelton, et al J. Ent. Sci 26:17). 4 ml of the diet is poured into 1 oz. clear plastic cups (Bioserve product #9051). 5 neonate *P. xylostella* from a diet adapted lab colony are placed in each diet containing cup and then covered with a white paper lid (Bioserve product #9049). 10 larvae are assayed per concentration. Trays of cups are placed in an incubator for 3 days at 72° F. with a 14:10 (hours) light: dark cycle. The number of live larvae in each cup is recorded.

Example 3

Results of Bioassays

The broth of *Xenorhabdus nematophilus* strain ATCC 19061 gives 100% mortality against *Plutella xylostella* (Px) in the insect bioassay of Example 2. Broth of each of *Xenorhabdus nematophilus* strain Ps1, *Xenorhabdus poinarii* strain ATCC 49122, and *Photorhabdus luminescens* strain Ps5, likewise gives 100% mortality against *Plutela xylostella* (Px) in the insect bioassay of Example 2.

Example 4

Construction of Cosmid Libraries

Total DNA is isolated from *Xenorhabdus nematophilus* strain ATCC 19061 by treating freshly grown cells resuspended in 100 mM Tris pH 8, 10 mM EDTA with 2 mg/ml lysozyme for 30 minutes at 37° C. Proteinase K is added to a final concentration of 100 μg/ml in 0.5% SDS and incubated at 45° C. The solution clears and becomes very viscous. The SDS concentration is increased to 1% and 300 mM NaCl and equal volume of phenol-chloroform-isoamyl alcohol are added. The sample is gently mixed for 5 minutes and centrifuged at 3K. This is repeated twice. The aqueous phase is then mixed with 0.7 volumes isopropanol and centrifuged. The DNA pellet is washed three times with 70% ethanol and gently resuspended in 0.5×TE. 6 µg of DNA are treated with 0.3 unit of Sau3A per µg of DNA at 37° C. for 3.5 minutes in a volume of 100 µl. The sample is then heated for 30 minutes at 65° C. to inactivate the enzyme, then incubated with 2 units of calf intestinal alkaline phosphatase for 30 minutes at 37° C. The sample is mixed with an equal volume of phenol-chloroform-isoamyl alcohol and centrifuged. The aqueous phase is removed and mixed with 0.7 volumes isopropanol and centrifuged. The pellet is resuspended in 0.5×TE at a concentration of 100 ng/ml.

SuperCos cosmid vector (Stratagene, La Jolla, Calif.) is prepared as described by the supplier utilizing the BamHI cloning site. Prepared SuperCos at 100 ng/ml is ligated with the *X. nematophilus* DNA previously digested with Sau3A at a ratio of 2:1 in a 5 µl volume overnight at 6° C. The ligation mixture is packaged using Gigapack XL III (Stratagene) as described by the supplier. Packaged phages are infected into XL-1 MR *E. coli* cells (Stratagene) as described by the supplier. The cosmid library is plated on L-agar with 50 μg/ml kanamycin and incubated 16 hours at 37° C. 500 colonies are patched to fresh L-kan plates at a density of 50/plate. The cells are washed off with L broth and mixed with 20% glycerol and frozen at −80° C.

In the case of the 4.2 Mb large genome of *X. nematophilus,* 450 clones with an average size of 40 Kb correspond to a 4-fold coverage of the genome. Therefore, screening of 450 clones should result in a 99% probability of finding any gene.

Cosmid libraries from *Xenorhabdus nematophilus* strain Ps1, Xenorhabdus poinariistrain ATCC 49122, and *Photorhabdus luminescens* strain Ps5 are constructed in a like manner.

Example 5

Results of the Cosmids Bioassays and Identification of Clones Having Insecticidal Activity 400 *E. coli* clones from each cosmid library are screened by insect bioassay yielding clones with activity against *Plutella xylostella.* An insecticidal cosmid clone from *Xenorhabdus nematophilus* strain ATCC 19061 is identified as pCIB9362. A 42 kb insecticidal cosmid clone from *Xenorhabdus nematophilus* strain Ps1 is identified as pCIB9379. A 42 kb insecticidal cosmid clone from *Xenorhabdus poinarii* strain ATCC 49122 is identified as pCIB9354. A 7 kb insecticidal cosmid clone from *Photorhabdus luminescens* strain Ps5 is identified as pCIB9383-21.

Example 6

Isolation of Subclones Having Insecticidal Activity

Clone pCIB9362 is digested with SacII and a 9 kb DNA fragment is isolated. This fragment is ligated into Bluescript cut with SacII. The ligation mixture is transformed into DH5α *E. coli* cells as described in Molecular Cloning, second edition (Sambrook et al.). The transformation mixture is plated on L agar plus 100 μg/ml ampillicin and incubated at 37° C. overnight. Isolated colonies are grown up in L broth with 100 μg/ml ampillicin and plasmid DNA isolated by alkaline minipreps as described in Molecular Cloning, second edition. The 9 kb SacII clone is identified as pCIB9362-3 and gives 100% mortality when bioassayed against *Plutella xylostella.* 3 μg of pCIB9362-3 is isolated, digested with 0.3 unit of Sau3A per μg DNA for 4, 6 and 8 min. at 37° C. and heated at 75° C. for 15 min. Samples are pooled and ligated into pUC19 previously digested with BamHI and treated with calf intestinal alkaline phosphatase. The ligation is transformed into DH5α *E. coli* cells, plated on L agar with Xgal/Amp as described in Molecular Cloning and grown overnight at 37° C. White colonies are picked and grown up in L broth with 100 μg/ml ampicillin and plasmid DNA is isolated as previously described. DNA is digested with EcoRI/HindIII and novel restriction patterns are sequenced. Sequencing primers are ordered from Genosys Biotechnologies (Woodlands, Tex.). Sequencing is performed using the dideoxy chain-termination method and is completed using Applied Biosystems Inc. model 377 automated DNA sequencer (Foster City, Calif.). The sequence is assembled using Sequencher 3.0 from Gene Codes Corporation (Ann Arbor, Mich.).

After identification of restriction sites and of potential ORF's, pCIB9362-3 is digested with ClaI and a 3.0 kb fragment is isolated cloned into Bluescript and transformed into DH5α *E. coli* cells. The isolated colonies are grown as previously described and plasmid DNA isolated by the alkaline method. The subclone is identified as pCIB9369 and gives 100% mortality against *Plutella xylostella* in a bioassay. pCIB9369 has been deposited on Nov. 12, 1997 and identified by NRRL Number B-21883 at the USDA ARS Patent Culture Collection.

A 20 kb fragment identified as pCIB9381 is subcloned from cosmid pCIB9379 using a NotI digest.

Example 7

Bioassay Results

Insect Bioassays are conducted for pCIB9369 for a variety of insects.

| Insect | pCIB9369 |
|---|---|
| *Plutella xylostella* | +++ |
| *Heliothis virescens* | na |
| *Helioverpa zea* | na |
| *Spodoptera exguia* | na |
| *C. elegans* | na | na = not active
\+ = significant growth inhibition
++ = >40% mortality, but less than 100%
+++ = 100% mortality These results show that the insecticidal toxin resulting from expression of the 3.0 kb nucleotide sequence in pCIB9369 is highly active against *Plutella xylostella.*

Bioassays for pCIB9381, pCIB9354, and pCIB9383-21 also show high insecticidal activity against *Plutella xylostella.*

Example 8

Size Fraction of the Insecticidal Activity

*Xenorhabdus nematophilus* cosmid clone pCIB9369 and Stratagene's Blue Script vector in *E. coli* host DH5 are grown in media consisting of 50% Terrific broth and 50% Luria broth, supplemented with 50 μg/ml of ampicilin. Shake flask cultures (300 ml in 1000 ml baffled flasks ) are grown at 250 RPM, overnight at 37° C. Cultures of each strain are centrifuged at 7,000 RPM in a Sorvall GS-3 rotor at 4° C. The pelleted cells are resuspended in 30 ml of 50 mM NaCl, 25 mM Tris base, pH 7.0. The concentrated cells are disrupted by sonication using a Branson Model 450

Sonicator for approximately eight 10 second cycles with cooling on ice between cycles. The sonicates are centrifuged in a Sorvall SS34 rotor at 6,000 RPM for 10 minutes at 4° C. The resultant supernatants are filtered through a 0.2μ filter. The pellets from the centrifuged sonicates are resuspended in 30 ml of 50 mM NaCl, 25 mM Tris base, pH 7.0.

The 3 ml fractions of the filtrates are applied to Bio-Rad Econo-Pac 10 DG columns that had been previously equilibrated with 10 ml of 50 mM NaCl, 25 mM Tris base, pH 7.0. The flow through collected during sample loading is discarded. The samples are fractionated with two subsequent additions of 4 ml each of the NaCl—Tris equilibration buffer. The first three fractions are saved for testing. The first fraction should contain all material above about 6,000 mol. wt. The subsequent fractions should contain material smaller than 6,000 mol. wt.

A sample of the sonicated filtrate and the resuspended pellet following sonication, are tested along with the three fractions from the 10 DG column for activity on *P. xylostella* neonates in surface contamination assays. The filtered supernatant of the sonicate and the first column fraction from the 9369 sample is highly active on *P. xylostella*. The second and third fractions from the 9369 sample are not active. None of the samples from the DH5a with the Blue Script pasmid culture have activity. These results suggest that the insecticidal activity encoded on *X. nematophilus* clone pCIB9369 as well as the homologues from pCIB9381, pCIB9354, and pCIB9383-21 are larger than 6,000 molecular weight.

Example 9

Stability of the Insecticidal Activity

A 300 ml of Luria broth supplemented with 100 μg/ml ampicillin is inoculated with pCIB9369 and grown over night at 37° C. The samples are placed in sterile 15 ml screw cap tubes and stored at 22° C. and 4° C. One sample is centrifuged and the supernatant removed, freeze dried and stored at 22° C. These samples are stored in these conditions for 2 weeks and then bioassayed against Px. The freeze dried material is resuspended in the same volume as prior to freeze drying the sample. All samples are resuspended by vortexing. Another sample is treated at 100° C. for 5 minutes.

| Treatment | Result |
|---|---|
| 22° C. (2 weeks) | ++ |
| 4° C. (2 weeks) | ++ |
| Freeze Dried (2 weeks) | ++ |
| 100° C. for 5 minutes | na | na = not active.

Example 10

Heat Inactivation of the Insecticidal Activity

The heat stability of the toxin is determined. Overnight cultures of the *E. coli* strain pCIB9369 (*E. coli* host DH5a, carrying the 3.0 kb DNA of *Xenorhabdus nematophilus*) are grown in a 50:50 mixture of Luria broth and terrific broth. Cultures are grown at 37° C. in culture tubes on a tube roller. Samples of one ml each of the culture are placed in a 1.5 ml eppendorf tube and placed at 60° C., 80° C. The samples are removed after five minutes and allowed to cool to room temperature. This sample along with an untreated portion of the culture is assayed on *P. xylostella.* 50 μl of sample of sample is spread on diet, allowed to dry and neonate larvae *P. xylostella* applied to the surface. The assay is incubated for 5 days at room temperature.

The untreated sample and the sample treated at 60° C. cause 100% mortality. The sample treated at 80° C. and a diet alone control do not cause observable mortality.

Example 11

Protease Treatment of the Insecticidal Activity

*Xenorhabdus nematophilus* cosmid clone pCIB9369 and Stratagene's Blue Script vector in *E. coli* host DH5 are grown in media consisting of 50% Terrific broth and 50% Luria broth, supplemented with 50 μg/ml of ampicilin. Shake flask cultures (300 ml in 1000 ml baffled flasks ) are grown at 250 RPM, overnight at 37° C. Cultures of each strain are centrifuged at 7,000 RPM in a Sorvall GS-3 rotor at 4° C. The pelleted cells are resuspended in 30 ml of 50 mM NaCl, 25 mM Tris base, pH 7.0. The concentrated cells are disrupted by sonication using a Branson Model 450 Sonicator for approximately eight 10 second cycles with cooling on ice between cycles. The sonicates are centrifuged in a Sorvall SS34 rotor at 6,000 RPM for 10 minutes at 4° C. The resultant supernatants are filtered through a 0.2μ filter. One ml samples of the supernatants are adjusted to 5mM Ca++ with the addition of $CaCl_2$. Protease K (Gibco BRL; Gaithersburg, Md.) is added to 500 μg/ml. Samples are incubated for 2 and 24 hr at 37° C. Control samples are prepared and incubated with added Ca++ but no protease.

The sonicate filtrate from pCIB9369 and the pCIB9369 samples incubated in the presence of 5mM Ca++ produce 100% mortality on *Plutella xylostella* neonate larvae. The pCIB9369 samples incubated with protease K in addition to Ca++ show slightly less mortality, approximately 90% mortality on Plutella.

Example 12

Sequence Comparisons with the Protein Sequence of cry3A and the Protein Sequence of a Juvenile Hormone Esterase The nucleotide sequence of pCIB9369 (SEQ ID NO:1) reveals two open reading frames (ORFs) at nucleotides 569–976 and 1045–2334. ORF #1 has no homology to any sequences in Genbank after a search with the UWGCG Blast and Gap programs. A Gap analysis of the protein encoded by ORF #2 of pCIB9369 by the Blast program identifies some insignificant homology (21 % identity) to *Bacillus thuringensis* cry3A protein. However, a Gap analysis of the protein encoded by ORF #2 of pCIB9369 (SEQ ID NO:3) by the Blast program does identify homology (30.6% AA identity and 44.1% AA similarity) to a juvenile hormone esterase-related protein (GenBank accession 2921553; Henikoff et al., *PNAS USA* 89: 10915–10919 (1992))

The nucleotide sequences of pCIB9381, pCIB9354, and pCIB9383-21 also reveal two open reading frames in each of these clones. The nucleotide sequences of the two ORFs in each of pCIB9381 and pCIB9383-21 are all over 90% identical to those in pCIB9369. Hence, the ORF #2 proteins of pCIB9381 and pCIB9383-21 have essentially the same homology to the juvenile hormone esterase-related protein as does the ORF #2 protein of pCIB9369. The nucleotide sequence of ORF #1 of pCIB9354 is 77% identical to the nucleotide sequence of ORF #1 of pCIB9369, and the nucleotide sequence of ORF #2 of pCIB9354 is 79% identical to the nucleotide sequence of ORF #2 of pCIB9369. The ORF #2 protein of pCIB9354 also has homology to the juvenile hormone esterase-related protein (29.2% AA identity and 42.2% AA similarity).

Example 13

Sequence Comparison of pCIB9369 and Sequences from WO 98/08388

Twenty-two sequences of 60 nucleotides each (60-mers) are derived from the 38.2 kb DNA fragment whose nucleotide sequence is described in WO 98/08388 and are compared to the nucleotide sequence of pCIB9362-3, which comprises pCIB9369. The first 60-mer starts at base 1 in the 38.2 kb DNA fragment, while the other 60-mers are located at approximately 2 kb intervals on the DNA fragment. Their positions on the 38.2 kb DNA fragment are listed below:

1–60; 2,041–2,100; 4,021–4,080; 6,001–6,060; 8,041–8,100; 10,021–10,080; 12,001–12,060; 14,041–14,100; 16,021–16,080; 18,001–18,060; 20,041–20,100; 22,021–22,080; 24,001–24,060; 26,041–26,100; 28,021–28,080; 30,001–30,060; 32,041–32,100; 34,021–34,080; 36,001–36,060; 38,041–38,100; 38,161–38,220.

The sequences are compared using UWGCG Gap program and each of the 22 60-mer sequences as well as their complementary sequences are tested. The results of these alignments indicate that the highest percentage of identity is 53%, which is not considered to be a significant homology in the art.

Example 14

Southern Blot Analysis using Probes Derived from WO 98/08388 Sequences

Pairs of oligonucleotides are designed to amplify DNA fragments of the 38.2 kb DNA fragment published in WO 98/08388. The oligonucleotides are ordered from Genosys Biotechnologies (The Woodlands, Tex.) and their positions in the 38.2 kb DNA fragment are indicated below. Also listed are their and the sizes of the amplified PCR fragments:

VK1046: positions 20–40
VK1047: positions 2,078–2,100
Size of the PCR fragment amplified using VK1046 and VK1047: 2,080 bp
VK1048: positions 11,221–11,241
VK1049: positions 13,360–13,380
Size of the PCR fragment amplified using VK1048 and VK1049: 2,120 bp
VK1050: positions 26,581–26,601
VK1051: positions 28,537–28,560
Size of the PCR fragment amplified using VK1050 and VK1051: 1,979 bp
VK1052: positions 18,901–18,921
VK1053: positions 20,321–20,340
Size of the PCR fragment amplified using VK1052 and VK 1053: 1,439 bp
VK1054: positions 34,261–34,281
VK1055: positions 35,320–35,340 BP
Size of the PCR fragment amplified using VK1054 and VK1055: 1,079 bp The PCR reactions are completed using a Perkin-Elmer 9600 Thermo-Cycler with the following conditions: 94° C., 2 min.; then 30 cycles at 94° C., 30 sec; 54° C., 30 sec; 72° C., 4 min. The samples contain 800 ng of *Xenorhabdus nematophilus* DNA, 0.1–0.5 $\mu$M of each pair of oligonucleotides, 250 $\mu$M dNTP, 5U Taq Polymerase and 1×buffer (Perkin-Elmer) in a final volume of 100 $\mu$l. The completed reactions are precipitated in ethanol, resuspended in TE and loaded on a 1 % SeaPlaque (FMC, Rockland, Me.) TBE gel. After electrophoresis, the fragments are cut out from the gel after ethidium bromide staining and visualization under UV light. The gel slices are melted at 65° C. and 10 $\mu$l aliquots are mixed with 10 $\mu$l distilled water, boiled for 5 min. and placed on ice. Then, 15 $\mu$l of Random Priming label buffer (GIBCO-BRL, Gaithersburg, Md.), 6 $\mu$l dNTP mix (without dCTP), 80 $\mu$Ci $\alpha$-dCT$^{32}$P and 1 $\mu$l Klenow are mixed. The labeling reaction is carried out during 60 min. at room temperature. The samples are cleaned up on Nick columns (Pharmacia Biotech) according to the supplier's recommendations. The probes are boiled for 5 min. and placed on ice.

A Southern blot is performed by digesting *Xenorhabdus nematophilus* total DNA, DNA derived from cosmids pCIB9362 and pCIB9363 (these cosmids overlap over 25 kb and both contain the DNA fragment of pCIB9369; pCIB9362 was used for subcloning), DNA derived from subclones pCIB9362-3 (9 kb SacII fragment) and pCIB9369 (2.96 kb ClaI fragment), digested with ClaI, SacI or HindIII. The digestion reactions are loaded on a 0.75% agarose TBE gel and run overnight. A picture is taken and the gel is treated as described by Bio-Rad for blotting to a Zeta-Probe hybridization membrane. After blotting, the membrane is baked at 80° C. for 30 min. The membrane is then placed in 7% SDS, 250 mM sodium phosphate, pH 7.2 and incubated at 67° C. for 30 min. Fresh solution is added and after equilibration to 67° C., the radioactive probes described above are added and allowed to hybridize overnight. The membrane is washed in 2×SSC, 0.5% SDS for 30 min. at 67° C. and then 0.5×SSC, 0.5% SDS for 30 min. at 67° C. The membrane is exposed on to a film for 1 hr and 3 hr. The film is developed and the results show that the PCR probes from the WO 98/08388 sequence do not hybridize to the DNA of the cosmids or the DNA of the subclones described in this invention. However, a strong hybridization signal is observed with *X. nematophilus* DNA.

These results corroborate the results of the sequence comparisons and show that clone pCIB9369 is different from the nucleotide sequence described in WO 98/08388.

B. Expression of the Nucleic Acid Sequences of the Invention in Heterologous Microbial Hosts Microorganisms which are suitable for the heterologous expression of the nucleotide sequences of the invention are all microorganisms which are capable of colonizing plants or the rhizosphere. As such they will be brought into contact with insect pests. These include gram-negative microorganisms such as Pseudomonas, Enterobacter and Serratla, the gram-positive microorganism Bacillus and the fungi Trichoderma, Giocladium, and *Saccharomyces cerevisiae*. Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum, Gliocladium virens,* and *Saccharomyces cerevisiae*.

Example 19

Expression of the Nucleotide Sequences in *E. coli* and Other Gram-Negative Bacteria Many genes have been expressed in gram-negative bacteria in a heterologous manner. Expression vector pKK223-3

(Pharmacia catalogue # 27-4935-01) allows expression in E. coli. This vector has a strong tac promoter (Brosius, J. et al., Proc. Natl. Acad. Sci. USA 81) regulated by the lac repressor and induced by IPTG. A number of other expression systems have been developed for use in E. coli. The thermoinducible expression vector $pP_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, expression of the nucleotide sequence in closely related gram negative-bacteria such as Pseudomonas, Enterobacter, Serratia and Erwinia is possible. For example, pLRKD211 (Kaiser & Kroos, Proc. Natl. Acad. Sci. USA 81: 5816–5820 (1984)) contains the broad host range replicon ori T which allows replication in many gram-negative bacteria.

In E. coli induction by IPTG is required for expression of the tac (i.e. trp-lac) promoter. When this same promoter (e.g. on wide-host range plasmid pLRKD211) is introduced into Pseudomonas it is constitutively active without induction by IPTG. This trp-lac promoter can be placed in front of any gene or operon of interest for expression in Pseudomonas or any other closely related bacterium for the purposes of the constitutive expression of such a gene. Thus, a nucleotide sequence whose expression results in an insecticidal toxin can therefore be placed behind a strong constitutive promoter, transferred to a bacterium which has plant or rhizosphere colonizing properties turning this organism to an insecticidal agent. Other possible promoters can be used for the constitutive expression of the nucleotide sequence in gram-negative bacteria. These include, for example, the promoter from the Pseudomonas regulatory genes gafA and lemA (WO 94/01561) and the Pseudomonas savastanoi IAA operon promoter (Gaffney et al., J. BacterioL 172: 5593–5601 (1990).

Example 20

Expression of the Nucleotide Sequences in Gram-Positive Bacteria

Heterologous expression of the nucleotides sequence in gram-positive bacteria is another means of producing the insecticidal toxins. Expression systems for Bacillus and Streptomyces are the best characterized. The promoter for the erythromycin resistance gene (ermR) from Streptococcus pneumoniae has been shown to be active in gram-positive aerobes and anaerobes and also in E. coli (Trieu-Cuot et al., Nucl Acids Res 18: 3660 (1990)). A further antibiotic resistance promoter from the thiostreptone gene has been used in Streptomyces cloning vectors (Bibb, Mol Gen Genet 199: 26–36 (1985)). The shuttle vector pHT31 01 is also appropriate for expression in Bacillus (Lereclus, FEMS Microbiol Lett 60: 211–218 (1989)). A significant advantage of this approach is that many gram-positive bacteria produce spores which can be used in formulations that produce insecticidal agents with a longer shelf life. Bacillus and Streptomyces species are aggressive colonizers of soils Example 21

Expression of the Nucleotide Sequences in Fungi

Trichoderma harzianum and Gliocladium virens have been shown to provide varying levels of biocontrol in the field (U.S. Pat. No. 5,165,928 and U.S. Pat. No. 4,996,157, both to Cornell Research Foundation). A nucleotide sequence whose expression results in an insecticidal toxin could be expressed in such a fungus. This could be accomplished by a number of ways which are well known in the art. One is protoplast-mediated transformation of the fungus by PEG or electroporation-mediated techniques. Alternatively, particle bombardment can be used to transform protoplasts or other fungal cells with the ability to develop into regenerated mature structures. The vector pAN7-1, originally developed for Aspergillus transformation and now used widely for fungal transformation (Curragh et al., Mycol. Res. 97(3): 313–317 (1992); Tooley et al., Curr. Genet. 21: 55–60 (1992); Punt et al., Gene 56: 117–124 (1987)) is engineered to contain the nucleotide sequence. This plasmid contains the E. coli the hygromycin B resistance gene flanked by the Aspergillus nidulans gpd promoter and the trpC terminator (Punt et al., Gene 56: 117–124 (1987)).

In a preferred embodiment, the nucleic acid sequences of the invention are expressed in the yeast Saccharomyces cerevisiae. For example, each of the two ORF's from pCIB9369, pCIB9381, pCIB9354, or pCIB9383 are cloned into individual vectors with the GAL1 inducible promoter and the CYC1 terminator. Each vector has ampicillin resistance and the 2 micron replicon. The vectors preferably differ in their yeast growth markers. The constructs are transformed into S. cerevisiae independently and together. The ORFs are expressed together and tested for protein expression and insecticidal activity.

C. Formulation of the Insecticidal Toxin

Insecticidal formulations are made using active ingredients which comprise either the isolated toxin or alternatively suspensions or concentrates of cells which produce it and which are described in the examples above. For example, E. coli cells expressing the insecticidal toxin may be used for the control of the insect pests. Formulations are made in liquid or solid form and are described below.

Example 18

Liquid Formulation of Insecticidal Compositions

In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethlene glycol ether (36 moles of ethylene oxide) | 5% | — | — |
| Tributylphenol polyethylene glyco ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |

-continued

| 2. Solutions: | a | b | c | d |
|---|---|---|---|---|
| Petroleum distillate (boiling range 160–190°) | — | — | 94% | — |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgit | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 19

Solid Formulation of Insecticidal Compositions

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |

-continued

| 2. Emulsifiable concentrate: | |
|---|---|
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 4% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

The insecticidal formulations described above are applied to the plants according to methods well known in the art, in such amounts that the insect pests are controlled by the insecticidal toxin.

D. Expression of the Nucleotide Sequences in Transgenic Plants

The nucleic acid sequences described in this application can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgtl1, λgtl0 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, PCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the nucleotide sequence of the invention confer insect resistance to the transgenic plants.

Example 22

Modification of Coding Sequences and Adjacent Sequences

The nucleotide sequences described in this application can be modified for expression in transgenic plant hosts. A host plant expressing the nucleotide sequences and which produces the insecticidal toxins in its cells has enhanced resistance to insect attack and is thus better equipped to withstand crop losses associated with such attack.

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (Science 261: 754–756 (1993)) have expressed the Pseudomonas nahG gene in transgenic plants under the control of the CaMV 35S promoter and the CaMV tmI terminator successfully without modification of the coding sequence and with x bp of the Pseudomonas gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the nucleotide sequence of this invention and the modification of these genes can be undertaken using techniques now well known in the art. The following problems may be encountered:

1. Codon Usage

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the E. coli uidA gene in plants. Further, Joshi (NAR 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes | | | | | | | | | | |
|---|---|---|---|---|---|---|---|---|---|---|
| | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Example 23

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter.

The following are non-limiting examples of promoters that may be used in expression cassettes.

a. Constitutive Expression, the Ubiquitin Promoter

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and Arabidopsis—Norris et al., Plant Mol. Biol. 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The Arabidopsis ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Inducible Expression, the PR-1 Promoter

The double 35S promoter in pCGN1761 ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1 a promoter is cleaved from plasmid pCIB1004 (for construction, see example 21 of EP 0 332104, which is hereby incorporated by reference) and transferred to plasmid pCGN1761ENX (Uknes et al., 1992). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761 ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tmI terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans,* the alcA gene encodes alcohol dehydrogenase 1, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6xGAL4/minimal promoter. Thus, tissue- or organ-specificity of the fusion protein is achieved leading to inducible tissue- or organ-specificity of the insecticidal toxin.

g. Root Specific Expression

Another pattern of gene expression is root expression. A suitable root promoter is described by de Framond (FEBS 290: 103–106 (1991)) and also in the published patent application EP 0 452 269, which is herein incorporated by reference. This promoter is transferred to a suitable vector such as pCGN1761 ENX for the insertion of a selected gene and subsequent transfer of the entire promoter-gene-terminator cassette to a transformation vector of interest.

h. Wound-Inducible Promoters

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wuni gene. Xu et al. show that a wound-inducible promoter from the dicotyledon potato (pin2) is active in the monocotyledon rice. Further, Rohrmeier & Lehle describe the cloning of the maize wuni cDNA which is wound induced and which can be used to isolate the cognate promoter using standard techniques. Similar, Firek et al. and Warner et al. have described a wound-induced gene from the monocotyledon *Asparagus officinalis,* which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression

Patent Application WO 93/07278, which is herein incorporated by reference, describes the isolation of the maize trpA gene, which is preferentially expressed in pith cells. The gene sequence and promoter extending up to –1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tmI terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 24

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. App. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below, the construction of two typical vectors suitable for Agrobacterium transformation is described.

a. pCIB200 and pCIB2001

The binary vectors pCIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglI, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives Thereof

The binary vector pCIB10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for Non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35 pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG1 9and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Example 25

Transformation

Once a nucleic acid sequence of the invention has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus Agrobacterium can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or micro-injection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Hofgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al.

Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of 1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using Agrobacterium has also been described. See, WO 94/00977 and U.S. Pat. No. 5,591,616, which are incorporated herein by reference.

3. Transformation of Plastids

Seeds of *Nicotiana tabacum* c.v. 'Xanthi nc' are germinated seven per plate in a 1" circular array on T agar medium and bombarded 12–14 days after sowing with 1 $\mu$m tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings are incubated on T medium for two days after which leaves are excised and placed abaxial side up in bright light (350–500 $\mu$mol photons/m$^2$/s) on plates of RMOP medium (Svab, Z., Hajdukiewicz, P. and Maliga, P. (1990) *PNAS* 87, 8526–8530) containing 500 $\mu$g/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual,* Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

E. Breeding and Seed Production

Example 26

Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding,* John Wiley & Sons, NY (1981); *Crop Breeding,* Wood D. R. (Ed.) American Society of Agronomy Madison, Wis. (1983); Mayo O., *The Theory of Plant Breeding,* Second Edition, Clarendon Press, Oxford (1987); Singh, D. P., *Breeding for Resistance to Diseases and Insect Pests,* Springer-Verlag, NY (1986); and Wricke and Weber, *Quantitative Genetics and Selection Plant Breeding,* Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 27

Seed Production

In seed production, germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods exemplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be designed for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a gene of the present invention that is expressed in said transformed plant at higher levels than in a wild type plant, together with a suitable carrier, together with label instructions for the use thereof for conferring broad spectrum disease resistance to plants.

The above disclosed embodiments are illustrative. This disclosure of the invention will place one skilled in the art in possession of many variations of the invention. All such obvious and foreseeable variations are intended to be encompassed by the appended claims.

What is claimed is:

1. An isolated nucleic acid molecule comprising a nucleotide sequence that encodes at least one toxin that is active against insects, wherein said nucleotide sequence:
    (a) has a compliment that hybridizes to a nucleotide sequence selected from the group consisting of: nucleotides 569–979 of SEQ ID NO:1 nucleotides 1045–2334 of SEQ ID NO: 1, SEQ ID NO:4, SEQ ID NO:6, SEQ ID NO:8, SEQ ID NO:10 SEQ ID NO:12, and SEQ ID NO:14 in 7% sodium dodecyl sulfate (SDS), 0.5 M NaPO$_4$, 1 mM EDTA at 50° C. with washing in 0.1×SSC, 0.1% SDS at 65° C.; or
    (b) is isocoding with the nucleotide sequence of (a); or
    (c) comprises a 20 base pair nucleotide portion identical in sequence to a consecutive 20 base pair nucleotide portion of a nucleotide sequence selected from the group consisting of: nucleotides 569–979 of SEQ ID NO: 1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO: 14.

2. An isolated nucleic acid molecule according to claim 1, wherein said nucleotide sequence is isocoding with a nucleotide sequence having a compliment that hybridizes to nucleotides 569–979 of SEQ ID NO 1, nucleotides 1045–2334 of NO:1, SEQ ID NO:4, SEQ ID NO:6, SEQ ID NO:8, SEQ ID NO:10, SEQ ID NO:12, or SEQ ID NO: 14 in 7% sodium dodecyl sulfate (SDS), 0.5 M NaPO$_4$, 1 mM EDTA at 50° C. with washing in 0.1×SSC, 0.1% SDS at 65° C.

3. An isolated nucleic acid molecule according to claim 1, wherein said nucleotide sequence has a compliment that hybridizes to nucleotides 569–979 of SEQ ID NO: 1, nucleotides 1045–2334 of SEQ ID NO: 1, SEQ ID NO:4, SEQ ID NO:6, SEQ ID NO:8, SEQ ID NO: 10, SEQ ID NO: 12, or SEQ ID NO: 14 in 7% sodium dodecyl sulfate (SDS), 0.5 M NaPO$_4$, 1 mM EDTA at 50° C. with washing in 0.1×SSC, 0.1% SDS at 65° C.

4. An isolated nucleic acid molecule according to claim 1, wherein said nucleotide sequence encodes an amino acid sequence selected from the group consisting of SEQ ID NOs:2, 3, 5, 7, 9, 11, 13, and 15.

5. An isolated nucleic acid molecule according to claim 1, wherein said nucleotide sequence comprises nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, or SEQ ID NO:14.

6. An isolated nucleic acid molecule according to claim 1, wherein said nucleotide sequence has a compliment that hybridizes to nucleotides 569–979 of SEQ ID NO:1, SEQ ID NO:4, SEQ ID NO:8, or SEQ NO:12 in 7% sodium dodecyl sulfate (SDS), 0.5 M $NaPO_4$, 1 mM EDTA at 50° C. with washing in 0.1×SSC, 0.1% SDS at 65° C.

7. An isolated nucleic acid molecule according to claim 1, wherein said nucleotide sequence encodes the amino acid sequence set forth in SEQ ID NO:2, SEQ ID NO:5, SEQ ID NO:9, or SEQ ID NO:13.

8. An isolated nucleic acid molecule according to claim 1, wherein said nucleotide sequence has a compliment that hybridizes to nucleotides 1045–2334 of SEQ ID NO: 1, SEQ ID NO:6, SEQ ID NO: 10, or SEQ ID NO: 14 in 7% sodium dodecyl sulfate (SDS), 0.5 M $NaPO_4$, 1 mM EDTA at 50° C. with washing in 0.1 ×SSC, 0.1% SDS at 65° C.

9. An isolated nucleic acid molecule according to claim 1, wherein said nucleotide sequence encodes the amino acid sequence set forth in SEQ ID NO:3, SEQ ID NO:7, SEQ ID NO:11, or SEQ ID NO:15.

10. An isolated nucleic acid molecule according to claim 1, wherein said nucleotide sequence comprises the approximately 3.0 kb DNA fragment comprised in pCIB9369 (NRRL B-21883).

11. An isolated nucleic acid molecule according to claim 1, wherein the toxin is active against *Plutella xylostella*.

12. An isolated nucleic acid molecule according to claim 1, wherein said nucleic acid molecule comprises a 20 base pair nucleotide portion identical in sequence to a consecutive 20 base pair nucleotide portion of a nucleotide sequence selected from the group consisting of: nucleotides 569–979 of SEQ ID NO:1, nucleotides 1045–2334 of SEQ ID NO:1, SEQ ID NO:4, SEQ ID NO:6, SEQ ID NO:8, SEQ ID NO:10, SEQ ID NO:12, and SEQ ID NO:14.

13. A chimeric gene comprising a heterologous promoter sequence operatively linked to the nucleic acid molecule of claim 1.

14. A recombinant vector comprising the chimeric gene of claim 13.

15. A host cell comprising the chimeric gene of claim 13.

16. A host cell according to claim 15, which is a bacterial cell.

17. A host cell according to claim 15, which is a yeast cell.

18. A host cell according to claim 15, which is a plant cell.

19. A plant comprising the plant cell of claim 18.

20. A plant according to claim 19, which is maize.

21. A method of producing a toxin that is active against insects, comprising:

(a) obtaining a host cell according to claim 15; and (b) expressing the nucleic acid molecule in said cell, which results in at least one toxin that is active against insects.

22. Seed from the plant of claim 19.

23. Seed from the maize plant of claim 20.

* * * * *